United States Patent [19]

König et al.

[11] 4,219,680

[45] Aug. 26, 1980

[54] PROCESS FOR OBTAINING PURE 2-(PERFLUOROALKYL)-ETHANOLS FROM THEIR MIXTURES WITH 2-(PERFLUOROALKYL)-ETHYLENES AND POSSIBLY 2-(PERFLUOROALKYL)-ETHYL ESTERS

[75] Inventors: Inge König, Mühldorf; Horst Streitberger, Altötting; Engelbert Krempl, Burgkirchen; Ulrich Schwenk, Burghausen, all of Fed. Rep. of Germany

[73] Assignee: Hoechst Aktiengellschaft, Fed. Rep. of Germany

[21] Appl. No.: 60,623

[22] Filed: Jul. 25, 1979

[30] Foreign Application Priority Data

Jul. 25, 1978 [DE] Fed. Rep. of Germany ....... 2832532

[51] Int. Cl.$^2$ .............................................. C07C 31/39
[52] U.S. Cl. ...................................... 568/842; 203/63; 203/64; 203/DIG. 6; 260/653.5; 560/236
[58] Field of Search .................... 568/842; 203/63, 64, 203/DIG. 6; 260/653.5

[56] References Cited

U.S. PATENT DOCUMENTS 3,283,012   11/1966   Day ...................................... 568/842

*Primary Examiner*—Howard T. Mars
*Attorney, Agent, or Firm*—Connolly and Hutz

[57] ABSTRACT

2-(perfluoroalkyl)-ethanols of the formula $R_fCH_2CH_2OH$ are obtained from 2-(perfluoroalkyl)-ethyl iodides of the formula $R_fCH_2CH_2I$ as a mixture with 2-(perfluoroalkyl)-ethylenes of the formula $R_fCH=CH_2$ and possibly also with 2-(perfluoroalkyl)-ethylcarboxylic acid esters of the formula $R_fCH_2CH_2O-COR$. From these mixtures, the 2-(perfluoroalkyl)-ethanols are obtained with a high purity degree when adding during the distillation separation as entrainer an alkanol having from 1 to 8 carbon atoms or a monoalkyl ether of ethyleneglycol the alkyl radical of which contains 1 to 4 carbon atoms, or a mixture of such alkanols and/or alkylglycols, and in the presence of 2-(perfluoroalkyl)-ethylcarboxylic acid esters, furthermore an acidic ester interchange catalyst.

2 Claims, No Drawings

PROCESS FOR OBTAINING PURE 2-(PERFLUOROALKYL)-ETHANOLS FROM THEIR MIXTURES WITH 2-(PERFLUOROALKYL)-ETHYLENES AND POSSIBLY 2-(PERFLUOROALKYL)-ETHYL ESTERS

The invention relates to a process for obtaining 2-(perfluoroalkyl)-ethanols of the formula $R_f$-$CH_2CH_2OH$ (hereinafter defined in abbreviated form as $R_f$ ethanols) from their mixtures with 2-(perfluoroalkyl)-ethylenes of the formula $R_f$-$CH=CH_2$ (hereinafter defined in abbreviated form as $R_f$ ethylenes), and possibly with 2-(perfluoroalkyl)-ethylcarboxylic acid esters of the formula $R_f$-$CH_2CH_2OCOR$ (hereinafter defined in abbreviated form as $R_f$ ethyl esters), in which formulae $R_f$ is a mixture of perfluoroalkyl radicals having from 4 to 24, preferably 4 to 16, carbon atoms, either branched with methyl in terminal position, or preferably linear, and R is hydrogen, an aliphatic or aromatic radical.

Starting products for the obtention of $R_f$ ethanols are the 2-(perfluoroalkyl)-ethyl iodides of the formula $R_f$-$CH_2CH_2I$, which for their part are prepared from perfluoroalkyl iodides of the formula $R_fI$ by addition of ethylene. The perfluoroalkyl iodides are formed in a telomerization reaction of a short-chain perfluoroalkyl iodide (perfluoromethyl, -ethyl, -propyl or -isopropyl iodide) with tetrafluoro-ethylene. For practical reasons, only the starting product and optionally the telomer portion having $R_f$ radicals of up to 3 carbon atoms is separated usually from the telomer mixture, while the remaining mixture is subjected, either totally or separated into large fractions (that is, in a broad chain distribution with respect to the $R_f$ radical) to further work-up (addition of ethylene and preparation of derivatives).

For the preparation of $R_f$ ethanols from $R_f$ ethyl iodides, several processes are proposed in which $R_f$ ethylenes are obtained as by-products, for example in German Offenlegungsschriften Nos. 23 18 677 and 23 18 941. Although formation of these $R_f$ ethylenes can be suppressed substantially, but not entirely, these processes are nevertheless very interesting, because the $R_f$ ethylenes can be worked up for their part, too. However, the essential condition is the separation of these two components, $R_f$ ethanols and $R_f$ ethylenes, in a substantially pure state.

In the processing according to German Patent No. 1 264 444 and German Offenlegungsschrift No. 23 18 941, $R_f$ ethyl esters formed by esterification of the $R_f$ ethanol with the carboxylic acid derivative present as reactant are obtained as by-products, in many cases even in very large amounts. These carboxylic acid derivatives may stem from carboxylic acids of various kinds (see German Patent No. 1 264 444, column 6, lines 38 to 56); preferably, they are derivatives of short chain alkanecarboxylic acids having an alkyl chain of from 1 to 4 carbon atoms. Since these $R_f$ ethyl esters reduce the yield of the intended $R_f$ ethanols, it is desirable to convert them to $R_f$ ethanols.

Separation of the mixtures of $R_f$ ethanols and $R_f$ ethylenes (for example by washing with water for eliminating water-soluble substances and subsequent separation of the $R_f$ ethylenes by fractional distillation) succeeds in a satisfactory manner when the two components are products of pure $R_f$ chain, that is, when they contain one single and identical $R_f$ radical.

When however employing, as described above, the usual telomerization products having $R_f$ chain fractions, separation by distillation is practically impossible, as shown by a comparison of the following boiling points:

| $R_f$ radical | $R_f$ ethanol b.p./12 mbar | $R_f$ ethylene b.p./12 mbar |
|---|---|---|
| $C_6F_{13}$— | 72°–77° C. | 20°–25° C. |
| $C_8F_{17}$— | 93°–98° C. | 35°–40° C. |
| $C_{10}F_{21}$— | 112°–120° C. | 65°–75° C. |
| $C_{12}F_{25}$— | 127°–137° C. | 95°–98° C. |

As results from this Table, $C_6F_{13}CH_2CH_2OH$ and $C_{10}F_{21}CH=CH_2$ on the one hand, and $C_8F_{17}CH_2CH_2OH$ and $C_{12}F_{25}CH=CH_2$ on the other hand each have about the same boiling range.

It is therefore the object of this invention to provide a process which ensures separation of such mixtures and simultaneously allows to convert the $R_f$ ethyl esters possibly present to $R_f$ ethanols.

In accordance with this invention, the above object is achieved by a process which comprises adding to the mixtures an alkanol having from 1 to 8 carbon atoms, or a monoalkyl ether of ethyleneglycol the alkyl radical of which contains 1 to 4 carbon atoms, or mixtures thereof as entrainer, and in the case of 2-(perfluoroalkyl)-ethyl carboxylic acid esters being present adding furthermore an acidic ester interchange catalyst, and subsequently eliminating selectively the 2-(perfluoroalkyl)-ethylenes by fractional distillation.

According to this operation mode of the invention, the $R_f$ ethanols remain as residue, while $R_f$ ethylenes and the alkanol of ethyleneglycol-monoalkyl ether added as entrainer are obtained in the distillate, from where they are isolated by precipitation with water and phase separation.

The choice of the alkanol or ethyleneglycol-monoalkyl ether used as entrainer for the $R_f$ ethylenes depends on the main portion (with respect to chain length of the $R_f$ radical) occurring in the components of the mixture. When $R_f$ radicals having a chain length of from about 6 to about 10 carbon atoms predominate, methanol, ethanol or isopropanol are preferably added as entrainer. In the case where in the mixture $R_f$ radicals having a chain length of more than 10 carbon atoms predominate, propanol or alkanols having from 4 to 8 carbon atoms or the monomethyl, monoethyl, monopropyl or monobutyl ethers of ethyleneglycol are preferably added. In order to ensure a better control of the entraining behavior, mixtures of the cited alkanols and/or glycol ethers may alternatively be used.

The ratio of alkanol or ethyleneglycol-monoalkyl ether added as entrainer to starting mixture may vary within wide limits, that is, from about 1:10 to 10:1 parts by volume, relative to the volume of the starting mixtures to be separated. A volume ratio of entrainer to starting mixture of from 1:5 to 5:1 is preferred. Amounts of entrainer larger than 10:1 may be employed but do not bring about any further advantage.

When the starting mixtures contain $R_f$ ethyl esters in addition to $R_f$ ethanols and $R_f$ ethylenes, an acidic ester interchange catalyst must be added in addition to the entrainer. As such an acidic ester interchange catalyst, there may be used concentrated sulfuric acid, phosphoric acid, an alkyl-, alkylaryl- or arylsulfonic acid, or an ion exchanger yielding acidic groups. The amount of acidic ester interchange catalyst required is from about 1 to 50 weight %, relative to the amount of $R_f$ ethyl ester present in the starting mixture.

For carrying out the process of the invention, the starting mixture to be separated and the entrainer are introduced into a distillation flask provided with an agitator and an effective distillation column which ensures the required separation efficiency. In order to reduce the total volume, part of the entrainer only may be introduced at the start, and the remainder may be added in portions during the distillation, while the acidic ester interchange catalyst is advantageously added at the start of the distillation. The mixture of entrainer and $R_f$ethylenes is then distilled off with agitation, while $R_f$ethyl ester possibly present is simultaneously transesterified.

When the starting mixture to be separated consists of $R_f$ethanols and $R_f$ethylenes only, it may be fed continuously together with the entrainer to a distillation column at the head of which the mixture of $R_f$ethylenes and entrainer is taken off and at the bottom of which the $R_f$ethanols are discharged.

The $R_f$ethanols of the residue are freed by distillation from small amounts of remaining entrainer. The ester interchange catalyst possibly remaining in this residue can be eliminated advantageously either by washing with water (acids) or filtration (acidic ion exchangers).

Since addition of ethylene to perfluoroalkyl iodides is a telomerization reaction, too, products of the formula $R_f(CH_2CH_2)_nI$ are formed, where n is 2 or greater than 2. Before the work-up, these products are generally eliminated by distillation, leaving only small amounts (up to a maximum 3 weight %) of compounds containing 2 added ethylene units, which are contained also in the components of the starting mixtures thus formed. However, these compounds do not disturb the separation.

The pure $R_f$ethanols and the $R_f$ethylenes obtained according to the process of the invention from the mixtures are interesting intermediate products for the manufacture of water- and oil-proofing and/or dirt-repellent textile finishing agents, and of additives for fire extinguishing products. For example, there can be prepared from the $R_f$ethanols the esters thereof with unsaturated carboxylic acids, especially acrylic or methacrylic acid, from which esters important textile finishing agents are obtained by polymerization.

The following Examples illustrate the invention.

EXAMPLE 1

For reaction with potassium acetate in ethanol at 200° C., a mixture of perfluoroalkylethyl iodides having the following chain distribution is used:

| | |
|---|---|
| $C_6F_{13}CH_2CH_2I$ | 48.3 wt. % |
| $C_8H_{17}CH_2CH_2I$ | 33.4 wt. % |
| $C_{10}F_{21}CH_2CH_2I$ | 13.0 wt. % |
| $C_{12}F_{25}CH_2CH_2I$ | 5.3 wt. % |

The resulting mixture is composed as follows:

| | |
|---|---|
| $R_fCH=CH_2$ | 19.5 wt. % |
| $R_fCH_2CH_2OCOCH_3$ | 62.0 wt. % |
| $R_fCH_2CH_2OH$ | 18.5 wt. % |

The chain distribution of the $R_f$radicals is identical to that indicated above for the $R_f$iodides. 500 g (310 ml) of this mixture are introduced together with 2 l of methanol and 10 g of concentrated sulfuric acid into a 4 liter-glass flask provided with agitator, thermometer and a 25 cm distillation column with distillation head. The contents of the flask are heated to boiling with agitation and refluxed for one hour. Subsequently, the methyl acetate (b.p. 57° C.) formed and the methanol containing the $R_f$ethylenes (bottom temperature 70° C. maximum) are distilled off.

By adding water to the distillate, 93 g of pure $R_f$ ethylene separate as lower phase.

The residue of the flask amounting to 407 g is washed by stirring three times with 2 l each of water at 70° C., so that it is free from methanol and sulfuric acid, and then distilled under reduced pressure without using a column.

There are obtained:

| | bottom temp. °C. | b.p. °C. | pressure mbar | amount g |
|---|---|---|---|---|
| first runnings | up to 80 | up to 70 | 10 | 4 (water) |
| main fraction | 80–170 | 70–135 | 10 | 395 |
| residue | | | | 8 |

Gas chromatography analysis of the main fraction yields:

| | |
|---|---|
| $R_fCH_2OH$ | 98.7 wt. % |
| $R_fCH=CH_2$ | 0.8 wt. % |
| $R_fCH_2OCOCH_3$ | 0.5 wt. % |

(chain distribution of the $R_f$radicals as indicated above)

EXAMPLE 2

A mixture of $R_f$ethylenes, $R_f$ethanols and $R_f$ethyl esters is used, 2 l of methanol are added, and the mixture is worked up as described in Example 1. However, instead of 10 g of concentrated $H_2SO_4$, 40 g of an acidic ion exchanger is used as ester interchange catalyst (trade name: Amberlyst® 15; manufacturer: Rohm & Haas, Philadelphia, U.S.A.).

The methanol is completely distilled off together with methyl acetate and the $R_f$ethylenes (maximum bottom temperature 120° C.). The $R_f$ethylenes are precipitated from the distillate by means of water, and they are free from $R_f$ethanols.

The ion exchanger is filtered off from the residue of the flask. This residue (410 g), according to gas chromatography, is composed as follows:

| | |
|---|---|
| $R_fCH_2CH_2OH$ | 98.6 wt. % |
| $R_fCH=CH_2$ | 0.8 wt. % |
| $R_fCH_2CH_2OCOCH_3$ | 0.6 wt. % |

(chain distribution of the $R_f$radicals as in the starting product).

EXAMPLE 3

For reaction with pottasium acetate in ethanol, a mixture of perfluoroalkylethyl iodides of the following chain distribution is used:

| | |
|---|---|
| $C_6F_{13}CH_2CH_2I$ | 41.4 wt. % |
| $C_8F_{17}CH_2CH_2I$ | 29.9 wt. % |
| $C_{10}F_{21}CH_2CH_2I$ | 17.9 wt. % |
| $C_{12}F_{25}CH_2CH_2I$ | 8.2 wt. % |

-continued

| | |
|---|---|
| $C_{14}F_{29}CH_2CH_2I$ | 2.4 wt. % |
| $C_{16}F_{33}CH_2CH_2I$ | 0.2 wt. % |

The resulting mixture is composed as follows:

| | |
|---|---|
| $R_fCH=CH_2$ | 19.0 wt. % |
| $R_fCH_2CH_2OCOCH_3$ | 62.0 wt. % |
| $R_fCH_2CH_2OH$ | 19.0 wt. % |

(chain distribution of the $R_f$ radicals as indicated above).

500 g (310 ml) of this mixture are introduced together with 2 l of n-butanol and 10 g of concentrated sulfuric acid into the apparatus as used in Example 1, which however, is provided in this case with a 50 cm distillation column and a reflux condenser.

The contents of the flask are refluxed with agitation, while in the phase separator the $R_f$ ethylenes separate as lower phase and n-butanol forms the upper layer. After a two hours' boiling, phase formation is complete.

In a further two hours, 90% of the butanol are distilled off (maximum bottom temperature 120° C.).

Analysis by gas chromatography shows that the butanol distillate consists of pure butanol, and the lower phase of 17 weight % of butanol, 4.7 weight % of butyl acetate and 78.3 weight % of $R_f$ ethylenes. The residue of the flask amounting to 410 g is washed free from acid by agitating three times with 1 liter of water each, and distilled under reduced pressure without using a column.

There are obtained:

| | b.p. °C. | pressure mbar | amount g |
|---|---|---|---|
| first runnings | up to 70 | 10 | 8 (butanol/water) |
| main fraction | 70–165 | 10 | 392 |
| residue | | | 10 |

Gas chromatography analysis of the main fraction gives:

| | |
|---|---|
| $R_fCH_2CH_2OH$ | 99.5 wt. % |
| $R_fCH=CH_2$ | 0.5 wt. % |

(chain distribution of the $R_f$ radicals as indicated above)

EXAMPLE 4

A mixture of 450 g of $R_f$ ethanols and 50 g of $R_f$ ethylenes ($R_f$ chain distribution as in Example 1; in total 300 ml) is used, and operations are carried out in the apparatus as described in Example 1, which is provided in this case with a 50 cm column.

After addition of 1 l of methanol, the mixture is refluxed with agitation, and subsequently the methanol is completely distilled off at a bottom temperature of up to 120° C. By addition of water to the methanol distillate, 48 g of $R_f$ ethylenes separate.

The residue of the flask consists of

| | |
|---|---|
| 99.2 wt. % | $R_fCH_2CH_2OH$ and |
| 0.8 wt. % | $R_fCH=CH_2$ |

EXAMPLE 5

A product obtained in the reaction of perfluoroalkyl iodides ($R_f$ chain distribution as in Example 1) with dimethyl formamide and water is used, which mixture consists of

| | |
|---|---|
| $R_fCH_2CH_2OH$ | 70 wt. % |
| $R_fCH_2CH_2OCHO$ | 20 wt. % |
| $R_fCH=CH_2$ | 10 wt. % |

($R_f$ chain distribution as in Example 1).

250 g (155 ml) of this mixture are refluxed for one hour with agitation together with 0.5 l of methanol and 2.5 ml of concentrated sulfuric acid. Subsequently, the methyl formate formed and the methanol containing the $R_f$ ethylenes are distilled off at a bottom temperature of up to 70° C.

By addition of water to the distillate, 24 g of pure $R_f$ ethylenes separate as lower phase.

The residue of the flask is washed free from methanol and acid with three times 250 ml each of water, and according to gas chromatography analysis, it consists of

| | |
|---|---|
| 99.3 wt. % | $R_fCH_2CH_2OH$ |
| 0.4 wt. % | $R_fCH=CH_2$ |
| 0.3 wt. % | $R_fCH_2CH_2OCHO$ |

($R_f$ chain distribution as indicated above).

EXAMPLE 6

The product of the reaction of perfluoroalkylethyl iodides (chain distribution as in Example 1) with p-toluenesulfonic acid and water is used, which mixture consists of

| | |
|---|---|
| $R_fCH_2CH_2OH$ | 92.0 wt. % |
| $R_fCH=CH_2$ | 8.0 wt. % |

($R_f$ chain distribution as in Example 1).

360 g (225 ml) of this mixture are refluxed with 0.3 l of methanol. Subsequently, the methanol is distilled off, while further 0.7 l of methanol are added via a dropping funnel.

At a bottom temperature of 120° C. the distillation is complete. By adding water to the methanol distillate, 28 g of pure $R_f$ ethylenes separate as lower phase. The residue of the flask amounting to 332 g consists of

| | |
|---|---|
| 99.2 wt. % | $R_fCH_2CH_2OH$ |
| 0.8 wt. % | $R_fCH=CH_2$ |

($R_f$ chain distribution as indicated above).

EXAMPLE 7

For reaction with dimethyl formamide and water, a mixture of perfluoroalkylethyl iodides having the following chain distribution is used:

| | |
|---|---|
| $C_6F_{13}CH_2CH_2I$ | 42.0 wt. % |
| $C_8F_{17}CH_2CH_2I$ | 28.2 wt. % |
| $C_{10}F_{21}CH_2CH_2I$ | 14.9 wt. % |
| $C_{12}F_{25}CH_2CH_2I$ | 8.7 wt. % |
| $C_{14}F_{29}CH_2CH_2I$ | 3.5 wt. % |

| | |
|---|---|
| -continued | |
| $C_{16}F_{33}CH_2CH_2I$ | 1.5 wt. % |
| higher homologs | |
| (up to $C_{24}F_{49}$) | 1.2 wt. % |

The mixture resulting from this reaction is composed as follows:

| | |
|---|---|
| $R_fCH_2CH_2OH$ | 77.4 wt. % |
| $R_fCH=CH_2$ | 10.7 wt. % |
| $R_fCH_2CH_2OCHO$ | 11.9 wt. % |

1000 g (625 ml) of this mixture, together with 400 g (416 ml) of ethyleneglycol-monomethyl ether (b.p. 124.5° C.) and 5 g of concentrated sulfuric acid, are introduced into a 2 liter-flask provided with agitator, thermometer and a 25 cm distillation column with phase separator. The contents of the flask are refluxed for one hour with agitation, while in the phase separator 100 g of pure $R_f$-ethylenes separate as lower phase. Subsequently, the glycol ether is completely distilled off at a bottom temperature of up to 130° C.

According to gas chromatography analysis, the glycol ether distillate contains some $C_6F_{13}CH_2CH_2OH$, which is obtained as lower phase by precipitation with water (40 g).

The residue of the flask is washed free from acids by stirring three times with 2 l of water each, and subsequently distilled under reduced pressure without using a column.

There are obtained:

| | b.p. °C. | pressure mbar | amount g |
|---|---|---|---|
| first runnings | up to 90 | 10 | 30 |
| main fraction | 90–145 | 10 | 770 |
| residue | | | 25 |

According to gas chromatography analysis, the main fraction consists of pure $R_fCH_2CH_2OH$.

The $R_f$ ethyl ester is completely converted to $R_f$ ethanol; the $R_f$ ethylene content is below the limit of detection. The $R_f$ chain distribution in $R_f$-ethanol, in the main fraction and in the residue corresponds (while taking into the account the portion passed over with the glycol ether distillate) to that of the starting product; the homologs having $R_f$ chains of 16 and more carbon atoms being found substantially in the residue.

EXAMPLE 8

The reaction product of perfluoroalkylethyl iodides ($R_f$ chain distribution as in Example 1) and potassium acetate in ethanol at 200° C. is used, which mixture consists of

| | |
|---|---|
| $R_fCH=CH_2$ | 19.0 wt. % |
| $R_fCH_2CH_2OCOCH_3$ | 62.0 wt. % |
| $R_fCH_2CH_2OH$ | 19.0 wt. % |

500 g (310 ml) of this mixture, together with 1 l of ethyleneglycolmonoethyl ether (b.p. 135° C.) and 5 g of concentrated sulfuric acid, are refluxed for 3 hours with agitation, the $R_f$-ethylene being separated thereby. Subsequently, 800 ml of the ethyleneglycolmonoethyl ether are distilled off under normal pressure, and the remaining 200 ml at 12 mbars (bottom temperature maximum 132° C.).

By adding water, 28 g of $C_6F_{13}CH_2CH_2O$ are separated from the glycol ether distillate as lower phase. The residue of the flask is washed free from glycol ether and acid by stirring twice with water at 70° C., and then distilled without using a column.

There are obtained:

| | b.p. °C. | pressure mbar | amount g |
|---|---|---|---|
| first runnings | up to 70 | 10 | 4.8 |
| main fraction | 70–121 | 10 | 347.0 |
| residue | | | 20.5 |

According to gas chromatography analysis, the main fraction consists of

| | |
|---|---|
| $R_fCH_2CH_2OH$ | 98.9 wt. % |
| $R_fCH_2CH_2OCOCH_3$ | 0.6 wt. % |

The content of $R_f$-ethylenes is below the limit of detection. ($R_f$ chain distribution as indicated above while taking into the account the portion passed over with the glycol ether distillate).

The gas chromatography analyses were carried out under the following conditions:
length of column: 3.65m, diameter 0.32cm, packed with Chromosorb$^{(R)}$ type WAW DMCS;
stationary phase: 10 weight % of vinylmethylsilicone (UCCW 82);
carrier gas: nitrogen, speed 20 ml/min.

What is claimed is:

1. A process for obtaining 2-(perfluoroalkyl)-ethanols of the formula $R_f$-$CH_2CH_2OH$ from their mixtures with 2-(perfluoroalkyl)-ethylenes of the formula $R_f$—$CH=CH_2$ and possibly with 2-(perfluoroalkyl)-ethylcarboxylic acid esters of the formula $R_f$—$CH_2CH_2OCOR$, in which formulae $R_f$ is a mixture of perfluoroalkyl radicals having from 4 to 24 carbon atoms, either branched with methyl in terminal position, or preferably linear, and R is hydrogen, an aliphatic or aromatic radical, which comprises adding to the mixtures an alkanol having from 1 to 8 carbon atoms, or a monoalkyl ether of ethylene-glycol the alkyl radical of which contains 1 to 4 carbon atoms, or mixtures thereof as entrainer, and in the case of 2-(perfluoroalkyl)-ethylcarboxylic acid esters being present adding furthermore an acidic ester interchange catalyst, and subsequently eliminating selectively the 2-(perfluoroalkyl)-ethylenes by fractional distillation.

2. The process as claimed in claim 1, which comprises adding the entrainer to the mixture to be separated in a volume ratio of from 1:10 to 10:1.

* * * * *